United States Patent
Lu et al.

(10) Patent No.: US 8,620,590 B2
(45) Date of Patent: Dec. 31, 2013

(54) DOSE SURFACE METHOD FOR DETERMINATION OF ANALYTE RATIOS

(75) Inventors: Yabin Lu, Pleasanton, CA (US); Roger Walker, Benicia, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 379 days.

(21) Appl. No.: 12/895,626

(22) Filed: Sep. 30, 2010

(65) Prior Publication Data

US 2012/0084010 A1 Apr. 5, 2012

(51) Int. Cl.
*G06F 7/00* (2006.01)

(52) U.S. Cl.
USPC .................. 702/19; 702/20; 703/11; 703/12; 703/13; 707/700

(58) Field of Classification Search
None
See application file for complete search history.

(56) References Cited

U.S. PATENT DOCUMENTS

| 6,436,721 | B1 | 8/2002 | Kuo et al. |
| 2004/0019431 | A1 | 1/2004 | Sterling et al. |
| 2005/0176089 | A1 | 8/2005 | Ehrlich |
| 2009/0024332 | A1 | 1/2009 | Karlov et al. |
| 2010/0049444 | A1 | 2/2010 | Likuski et al. |

OTHER PUBLICATIONS

International Application No. PCT/US2011/54136, International Search Report and Written Opinion mailed on Feb. 14, 2012, 13 pages.

*Primary Examiner* — Mary Zeman
(74) *Attorney, Agent, or Firm* — Kilpatrick Townsend & Stockton, LLP; David B. Raczkowski

(57) ABSTRACT

Methods, systems, and apparatus for accurately determining a proportion (ratio) of two analytes is provided, as well as provide a concentration of a first analyte from a determined concentration of a second analyte and from a proportion of the analytes to each other. In one aspect, a surface model (called a "dose surface" herein) relating the concentrations of the two analytes to the proportion can be used to obtain accurate values for one of the variables (e.g. a concentration or the proportion) when the other two variables have previously been obtained. The dose surface can be a three-dimensional surface and be non-linear. The dose surface model can include multiple regression functions. For example, measured responses can be individually converted to concentrations using two dose-response curves, and the concentrations can be input to a dose surface function to obtain the proportion.

13 Claims, 11 Drawing Sheets

| Quantitation Criteria | Response Surface | | Dose Surface | |
|---|---|---|---|---|
| | Exp1 | Exp2 | Exp1 | Exp2 |
| 1.96STD (95% CI) | 0.30 | 1.08 | 0.33 | 0.28 |
| Average % Error | 1.61 | 3.56 | 1.75 | 2.31 |
| % of Patient with less than 10% error | 100 | 94 | 100 | 100 |
| %A1c dose replicate CV | 1.22 | 1.05 | 1.18 | 0.76 |
| Grand Mean | 0.00 | 0.23 | 0.03 | -0.23 |

FIG. 6

DOSE SURFACE METHOD FOR DETERMINATION OF ANALYTE RATIOS

CROSS-REFERENCES TO RELATED APPLICATIONS

This application is related to commonly owned U.S. patent application Ser. No. 12/196,132 entitled "Response Surface Method for Determination of Analyte Ratios" by Robert K. Likuski et al., filed Aug. 21, 2008, the disclosure of which is incorporated by reference in its entirety.

BACKGROUND

The present invention relates generally to a method for analyzing analytes in a biological sample, and more specifically to determining a relative proportion (also called a ratio herein) of concentrations of analytes in a biological sample.

Computing the ratio of two or more analytes in a sample is a useful comparison in a variety of contexts. Ratios are frequently used to compensate for variability in the composition or concentration of the analytes in a sample. For example, when measuring analytes present in urine, the concentration of analytes in any given sample can vary significantly. These concentration fluctuations can be normalized by creating a ratio between different analytes present in a sample. For example, a ratio can be created between the concentration of a urinary analyte and the concentration of creatinine in urine. Creating this relationship between two analytes in the sample allows for a more meaningful measurement in light of the concentration fluctuations. It is also possible to normalize the concentration of a desired analyte in tissue against the concentration of total protein or a specific protein such as, for example, albumin. Ratios can also compensate for correlated errors in the measurement, e.g., dilution errors.

One context for computing a ratio is the determination of percent hemoglobin A1c (HbA1c). HbA1c is the amount of glycated hemoglobin in a blood sample. The percent HbA1c can be obtained from a proportion of the concentration of HbA1c to the concentration of total hemoglobin. Percent HbA1c is useful in determining a response to therapy in diabetics, and also for diagnosing diabetics.

Reference methods to determine the ratio are not practical for general diagnosis, due to cost and speed. Common methods for determining a ratio between two analytes (e.g. for diagnosis) are often complicated to determine and/or inaccurate. For example, dividing one concentration by the other concentration provides inaccurate results, e.g., as interactions between analytes are ignored. For instance, in some measurement techniques, such as immunoassay, the first antibody used to measure the first analyte response may also interact with the second analyte in the sample.

Therefore, it is desirable for new methods, systems, and apparatus for determining a proportion of two analytes to each other in an efficient and accurate manner.

BRIEF SUMMARY

Accordingly, some embodiments of the present invention can provide methods, systems, and apparatus for determining a proportion (ratio) of two analytes accurately. Other embodiments can provide a concentration of a first analyte from a determined concentration of a second analyte and from a proportion of the analytes to each other. In one aspect, a surface model (called a "dose surface" herein) relating the concentrations of the two analytes to the proportion can be used to obtain accurate values for one of the variables (e.g. a concentration or the proportion) when the other two variables have previously been obtained. In various embodiments, the dose surface can be a three-dimensional surface and be non-linear.

In some embodiments, a "dose surface" method utilizes both the individual dose-response curves (relating a signal from a measuring device to a concentration) for each analyte and a three-dimensional calibration dose surface. The individual concentrations (or doses) for the dose surface model can be calculated from the responses via their respective dose-response curves. The analyte ratio can then be calculated via a three-dimensional "dose surface" which directly determines the final dose ratio from the calculated doses. Thus, in one embodiment, using a dose-surface regression model, the dependent variable is the ratio, and the two independent variables are the converted "dose" variables from the two measured responses obtained from the two individual curves. In various embodiments, the determined analyte doses can be used either directly as input to the surface model or alternately as mathematically transformed doses (e.g. fixed mathematical transformations that create a new concentration variable from the dose output from a dose-response curve). Examples of a mathematical transformation include plus, minus, multiplication, division, and exponential to the power of a real number. These transformations do not have variables (e.g. coefficients) that result from a functional fitting process.

According to one embodiment, a method of obtaining a property of a biological sample is provided. Two values are received. These two received values are one of three values: a first concentration for a first analyte of a biological sample, a second concentration for a second analyte of the biological sample, and a proportion of the two analytes of the biological sample. A non-linear function that maps the two concentrations to the proportion of the concentrations is received. A computing system calculates the third value of the group using the non-linear function and the two obtained values.

According to another embodiment, a method of calculating a regression model that is operable to determine a proportion of two analytes based on a measured response of each analyte is provided. Properties of a plurality of calibration samples are used. For example, a first concentration for a first analyte, a first response for the first analyte, a second concentration for a second analyte, a second response for the second analyte, and a proportion of the two analytes are received. A first dose-response curve is determined by fitting a first regression function to data points that include the first response and first concentration of each calibration sample. A second dose-response curve is determined by fitting a second regression function to data points that include the second response and second concentration of each calibration sample. New concentrations are determined from the respective dose-response curves. A dose surface model is determined by fitting a third regression function to data points including the third concentration, the fourth concentration, and the proportion.

Other embodiments are directed to systems and computer readable media associated with methods described herein.

As used herein, the term "function" refers to a mathematical relationship between one or more input variables and an output variable. A function can have one or more terms separated by a plus, a minus, a multiplication or a division sign. A term of a function can include any mathematical operator, and can include just one or many input variables. As used herein, the terms "proportion" and "ratio" refers to any value that conveys a relative amount of one variable to the amount of another variable. In one embodiment, the ratio may include a simple quotient of the two variables, and can also include other terms with different mathematical relationships besides a quotient (e.g. terms with just one variable). As used herein, the term "non-linear" refers to a function that has at least one term with a dependence on the input variables that is different from a linear relationship. For example, a ratio of X/Y is linear as both variables appear with a power of "1". A non-linear relationship has at least one variable that appears with a power other than "1" or "−1", such as 0.4, 2, −0.7, etc. As used herein, the term "concentration" can refer to any absolute physical amount (e.g. mass or volume) or relative amount (e.g. mass per volume) of a substance.

A better understanding of the nature and advantages of the present invention may be gained with reference to the following detailed description and the accompanying drawings.

BRIEF DESCRIPTION OF THE DRAWINGS

FIG. 6 is a table showing numerical results of a response surface method and a dose surface method according to embodiments of the present invention.

DETAILED DESCRIPTION

Standard/reference methods to determine a proportion (also called a ratio herein) of two analytes in a biological sample are slow and/or expensive to run. Faster and cheaper methods exist, but are less accurate and/or difficult to implement. Certain embodiments of the present invention use a dose surface model that relates determined concentrations of two analytes to the actual ratio of the amounts of the two analytes. In one embodiment, a two-step regression process is used. A first step utilizes doses calculated individually for each analyte via a regression model (dose-response curve). The ratio of analytes can then be calculated in the second step using the intermediate doses as variables in a different regression model.

I. Overview

Figure 1:
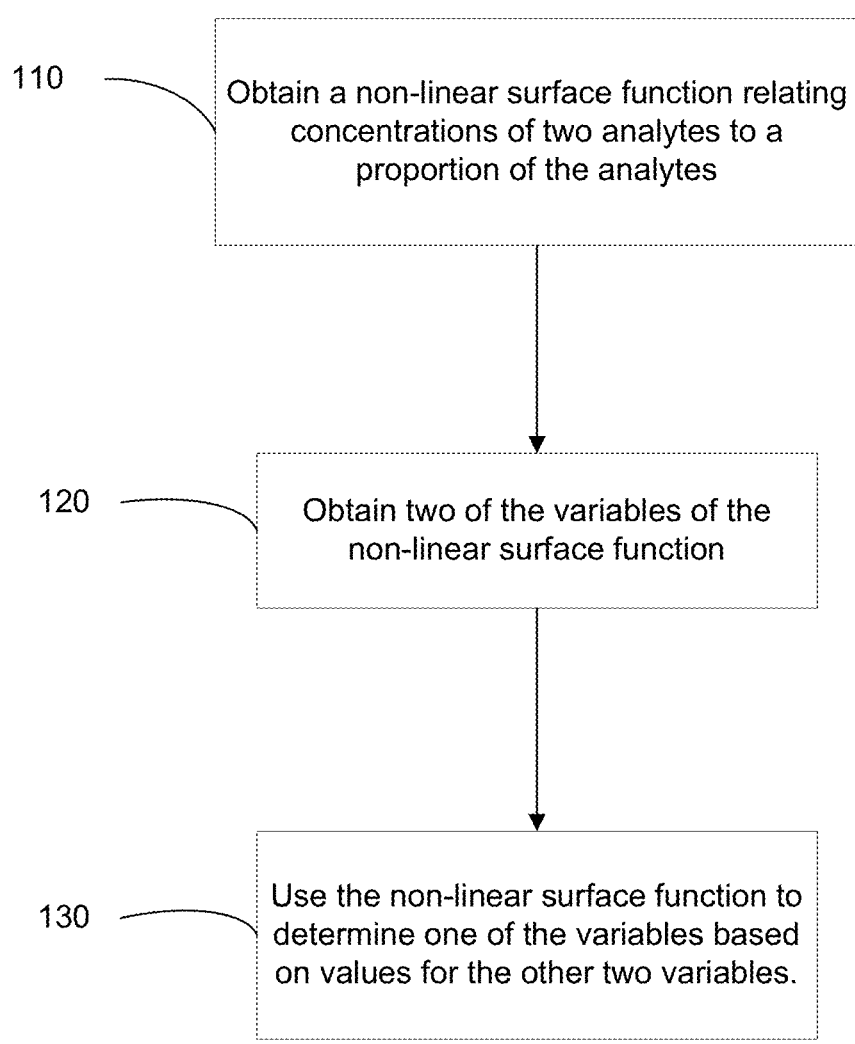
FIG. 1 is a flowchart illustrating a method of determining a property of a biological sample according to embodiments of the present invention.

FIG. 1 is a flowchart illustrating a method 100 of determining a property of a biological sample according to embodiments of the present invention. Method 100 can be used to determine a proportion of the amounts of two analytes in the biological sample. The amounts can initially be obtained as concentrations, and the proportion can be obtained from concentrations. Method 100 can also be used to obtain a concentration from the proportion and the other concentration. Method 100 and any other method described herein can be performed on a computer system.

In step 110, a non-linear surface function relating concentrations of two analytes to a proportion of the analytes is obtained. The surface function is a model that approximates the relationship between the two concentrations (doses) and the proportion. Thus, the surface function can map any two of these values to the third value. This model function can be created from data points obtained from calibration samples with known concentrations and proportion values. In one aspect, the model is a surface model as it is three-dimensional, with two dimensions being the concentrations and the third dimension being the proportion. In another aspect, the model is non-linear in that at least one term in the function is non-linear, as is defined above. In one embodiment, the dose surface function can be calculated. In another embodiment, the dose surface function can be read from a computer readable medium by a processor.

In step 120, two of the variables of the non-linear surface function are obtained. For example, the concentrations could be obtained or one concentration and the proportion could be obtained. In some embodiments, a concentration could be obtained by measuring a response signals from an experiment, where the response signal conveys information that can provide the concentration. In one embodiment, the response signal can be mapped to a concentration using a function (dose response curve) that is derived from data points obtained from calibration samples with known concentrations. In other embodiments, a concentration or a proportion can be measured directly by a user, or be known as the sample is a reference sample that is made to particular specifications or has been measured by another party.

In step 130, the non-linear surface function is used to determine one of the variables based on values for the other two variables. For example, if the concentrations are obtained for the two analytes, then the proportion can be obtained from the surface function. The two concentration values can be input into the formula defining the surface function, thereby outputting the proportion. As another example, the surface function can similarly be used to output one concentration value by inputting the proportion and the other concentration value. In one embodiment, the formula defining the surface function is rearranged to provide the particular concentration value as an output. In one aspect, the determined variable provides a property of the sample under test. The determined variable can provide diagnostic information, such as a likelihood of responding to particular therapies or whether someone likely has a particular disease or condition.

The use of a "dose surface" method can provide an advantage over simply dividing the concentrations to obtain a quotient and using the quotient as the ratio. Such a quotient method does not account for interactions between the two analytes that are components of the ratio. For example, these interactions can occur particularly at high concentrations of one or both analytes. In these cases, the surface corrects for these interactions and provides a more accurate value for the ratio.

The use of a "dose surface" method can also provide advantages over a "response surface" method that maps signal responses to a ratio of the analytes, whereas a dose surface method maps concentrations to a ratio of the analytes. A response surface method that utilizes a single regression model may work well when the dose and the response have a simple polynomial relationship; however, such a response surface method can be less effective when the dose-response relationship is more complicated, such as an exponential or kinetic relationship. In the latter case, it can be hard to keep the "response surface" model in a polynomial form, because the model potentially requires an excessive number of terms and coefficients.

Accordingly, a benefit of using a dose surface model with the concentrations is that the surface function can be simpler while maintaining accuracy. Thus, in some embodiments, fewer terms can be used. Also, the non-linear function can be smoother (e.g. lower frequencies), thereby providing greater accuracy in determining one of the variables.

The "response surface" model can also be less flexible in adjusting to changes in experimental conditions. Whereas, a "dose surface" method" can effectively have two parts, two dose-response curves being a model of a first part and and the dose surface function being the model of a second part. The coefficients of the two dose-response curves can be determined each time the calibrators are run. The two regression models that fit the two dose-response curves can be changed based on the changes in characteristic of the dose response relationship under different experimental conditions. Therefore, the method of determining a ratio can be modified according to the changes in experimental conditions.

In various embodiments, functions representing relationship between variables can have multiple terms, each with a different functional form. For example, different functional forms can include polynomial (which may be defined via interpolation or least squares), other types of power functions besides polynomial, exponential functions, or any suitable functional form.

II. Creation Of Dose Surface Model

Figure 2:
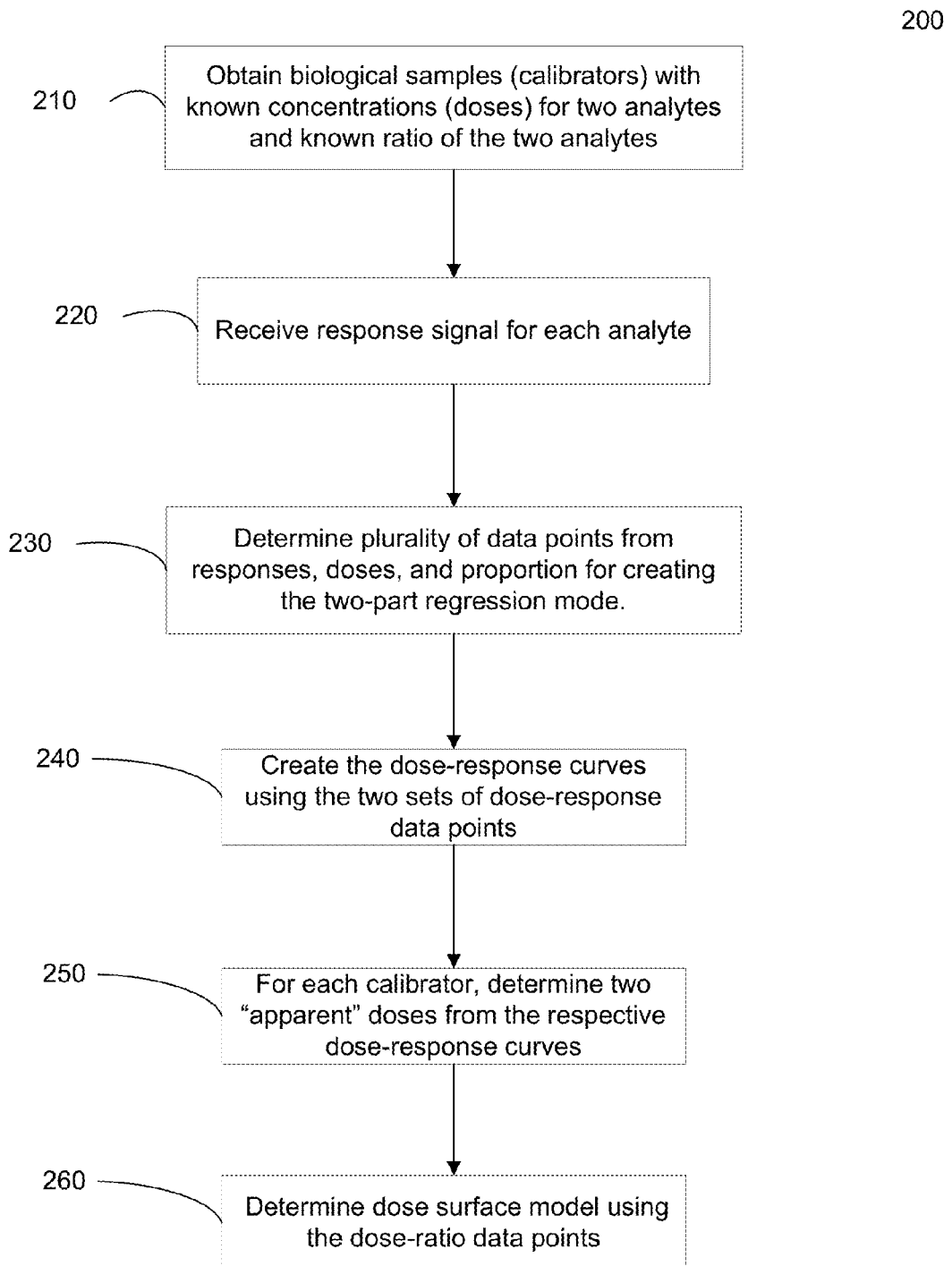
FIG. 2 is a flowchart of a method for obtaining a dose surface model according to embodiments of the present invention.

FIG. 2 is a flowchart of a method 200 for obtaining a dose surface model according to embodiments of the present invention. In one embodiment, method 200 can be performed by an end user who is actually performing the analysis of patients (e.g. humans or other animals). In another embodiment, method 200 can be performed by a party who provides an apparatus (e.g. computer code and/or a machine with computer code). One or more steps of method 200 can omitted, e.g., just step 260 can just use the values obtained in step 210, and the other steps can be omitted. One embodiment of method 200 uses a multi-part regression model.

In step 210, a plurality of biological samples with known concentrations for two analytes and known ratio of the two analytes are obtained. These biological samples are called calibration samples herein since they are used to calibrate the regression models. In one embodiment, the calibration samples can be obtained from a third party that produces biological samples with known concentrations of a plurality of analytes and known proportion of the analytes to each other. In another embodiment, the concentrations and proportion of the calibration samples can be determined directly (e.g. not through a regression model) by measuring the concentrations and proportions using standard or reference methods defining these values, such as such as optical density measurement, HPLC (High Performance Liquid Chromatography) measurement, or a Mass spectrometry measurement.

In one embodiment directed to %A1c, the concentration of total Hb can be determined directly by 1) absorbance measurement at a specific wavelength such as 405 nm , or 2) absorbance measurement of an alkaline hematin derivative at 650 nm, which are most commonly done with whole blood samples. In another embodiment, an international reference method for determining percent A1c proportion utilizes a complicated procedure in which the terminal peptide portion of the hemoglobin beta chain is cleaved enzymatically to yield glycated and nonglycated hexapeptides, which are first purified by HPLC, and then then resolved and measured by mass spectrometry or resolved by capillary electrophoresis followed by UV detection. Such a method is not practical for routine use, and is more suitable for generating reference samples with defined percent A1c values. The hemoglobin A1c mass (mg/mL) can be defined from values for the percentage of total hemoglobin and the concentration of total hemoglobin.

The standard methods for determining the proportion directly would not be practical for general use because they are too complicated, require highly trained personel, are too expensive, etc (as opposed to immunoassay tests, which are suitable for general use). In another embodiment, the sample can be created with a particular process such that the concentrations and proportion have predetermined values. For example, a mass spectrometry measurement could be used as a reference method (or other mesurement method) to ensure that a particular %A1c (the ratio of the hemoglobin A1c and the total hemoglobin) is achieved.

In step 220, a response signal is received for each analyte. In some embodiments, the response signals may be measured using a particular method (e.g. immunoassay) that is to be used in production runs for analyzing patient samples. The particular methods are ideally faster and cheaper than the reference methods that can be used to determine the concentrations and proportion values. In one embodiment, each analyte is measured independently, resulting in two measured responses, one for each analyte, from the two assays.

In step 230, a plurality of data points are determined for creating a two-part regression model for a dose surface model according to an embodiment. The data points can include dose-response data points for the first regression models and dose-ratio data points for the second regression model. A plurality of calibration samples can be used to obtain data points that span the range of concentration and propoprtion values that might be expected in non-reference samples.

A first set of dose-response data points include the response of the first analyte and the concentration of the first analyte. A second set of dose-response data points include the response of the first analyte and the concentration of the first analyte. These sets of dose-response data points can be considered two-dimensional data points (response, dose), which can be used to determine a regression function (dose-response curve) that approximates the behavior of the signal response to the concentration.

Additionally, the dose-ratio data points can be considered three-dimensional data points (dose 1, dose 2, proportion). In one embodiment, the dose 1 and dose 2 variables are the output of the respective dose-response curves. Thus, the dose variables that are used to determine the dose surface model may be different than the actual concentrations of the calibration sample. In another embodiment, the dose 1 and does 2 variables can be the actual concentrations of the calibration sample.

In step 240, the two sets of dose-response data points are used to create the dose-response curves. In some embodiments, multiple functional forms for the regression models of the dose-response curves can be tested. In one embodiment, the two regression models that best fit the relationship between the doses and the responses of the calibrators for each analyte, are generated. The coefficients of the different regression models can be varied to determine the best fit, e.g. using least squares. One skilled in the art will be familiar with the variety of ways of performing a functional fit to a set of data points. In one aspect, the coefficients can be independent of the final ratio of the analytes as the ratio is not used to determine the dose-response curves.

These first step regression models (dose response curves) can be, for example, a polynomial regression, an exponential, power function, reverse four-parameter logistic function (4PL), or any other regression models that best fits the analyte doses and their corresponding responses. The formula of the regression model for the dose-response curves can be modified based on the characteristics of each calibration run. In one embodiment, the responses can be mathematically transformed to obtain new variables (e.g. scaled, shifted, or combined with other responses) to obtain new varaibles for which the regression model is calculated. In another embodiment, the regression model can include such transformations.

In step 250, for each calibrator, two "apparent" doses are calculated from the two dose-response curves. In one embodiment, these "apparent" doses are used in the dose-ratio data points as mentioned above. Although this calculated analyte dose may not exactly match the true dosage that defines the ratio, it can be a variable more closely related to the true dose variable defined by the standard method. Therefore, the surface model can be much simpler. By linking the ratio directly to the two doses rather than the measured responses, the current dose surface model dramatically reduces the lack of fit error.

Accordingly, in some embodiments, the concentrations obtained from the dose response curves are used as the input variables (as opposed to the known concentration values, which may differ from those obtained from the dose response curves). For example, a sample may have a first signal response that corresponds to a first concentration according to a first dose-response curve. The sample may have a different known concentration, as the dose-response curve may not provide the exact known value. The same may be true for a second concentration. The concentrations derived from the dose-response curves can then be used as two of the data points for determing the non-linear surface function. In other embodiments, the actual concentrations values could be used.

In step 260, the dose surface model is determined using the dose-ratio data points. Thus, in one embodiment, a third regression model is established between the ratio and the calculated doses. In another embodiment, the two "apparent" doses can be transformed using a fixed transformation to create new input variables for determining the dose surface model. In one aspect, this second step regression can be a multivariate-regression that uses dose values calculated from one or more separate regression models in which the analyte responses are variables. The best functions for either regression model can be determined by trial and error, or by an automated method. In one embodiment, the formula for the regression model of the dose surface model can be modified based on analysis of variance.

In one embodiment, in addition to the regression coefficients for each analyte, the regression model itself for the dose response curves can be modified to provide more flexibility for the dose-based surface regression method in adapting to changes in experimental conditions. In one aspect, utilizing the two dose-response curves in the dose surface model allows all the regression coefficients of the three models to be determined and utilized simultaneously without increasing the number of calibrators. Additionally, since all the parameters or coefficients of both the dose surface model and the two regression models of the two curves can be simultaneously determined using the same set of calibrators, some embodiments can improve the efficiency of calibrator usage, reduce the number of calibrator required, and increases the amount of parameters defining the entire model.

III. Use Of Dose Surface Model

Figure 3:
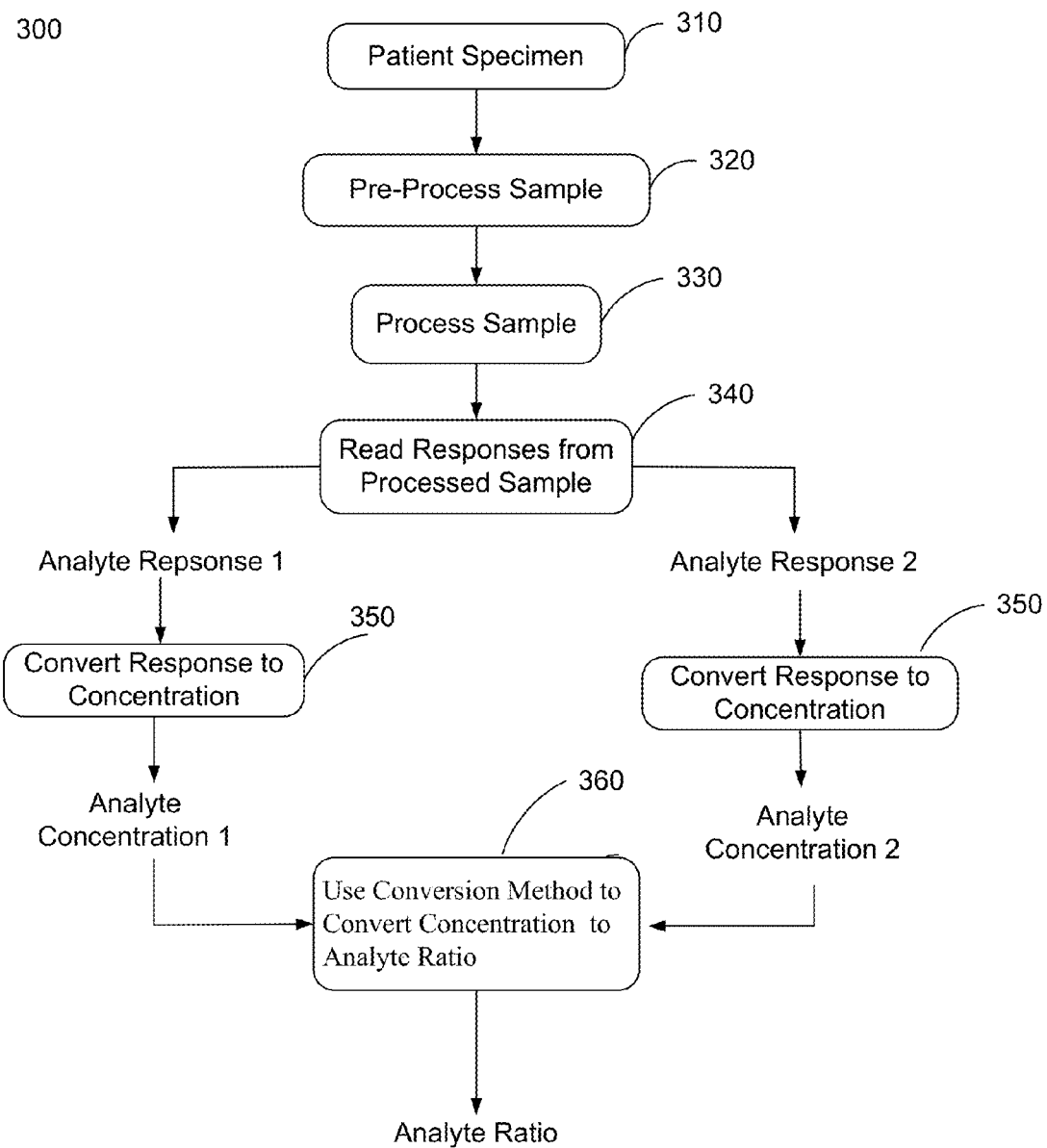
FIG. 3 is a flowchart of a method for determining an analyte ratio of a biological sample according to embodiments of the present invention.

FIG. 3 is a flowchart of a method 300 for determining an analyte ratio of a biological sample according to embodiments of the present invention. In one embodiment, method 300 can use the regression models obtained via any of the embodiments of method 200. Certain steps of method 300 are optional.

In step 310, a specimen (biological sample) is taken from a patient. Example specimens include blood, urine, or other bodily fluids. The specimen forms the basis for the sample from which a ratio of analytes can be measured and computed. The specimen does not necessarily have to come directly from a patient, e.g., the specimen may be available from another source.

In step 320, the specimen is converted into a pre-processed sample. A pre-processed sample can also be referred to as a test sample. This step may consist of anything done to the specimen before any analyte measurements are taken. For example, in certain embodiments, the specimen may be sampled and diluted by a specific amount. In other embodiments, an anti-coagulant may be added to the specimen. This step is optional as there may be times when the entire unaltered specimen will be used as the pre-processed sample.

The sample is measured in steps 330 and 340. In these two steps, the quantities of interest in the sample are presented as responses. Step 330 can include all the processing done by the instrument to ready the pre-processed sample for reading. Processing the sample can involve a variety of steps. Using a multi-analyte sandwich immunoassay as an example, the sample is reacted with antibodies or specific binding reagents attached to a solid phase, the solid phase is washed to remove unbound material, reacted with one or more labeled antibodies or binding reagents, and washed to remove unbound labeled reagent for subsequent reading of the response. Other examples include high-performance liquid chromatography (HPLC), immunoassay, plasmon resonance, electrophoresis, capillary electrophoresis, ultra-violet/visible/infrared spectroscopy, raman spectroscopy, surface enhanced raman spectroscopy, mass spectroscopy, gas chromatography, or others. There may be instances when no processing steps need to be taken on the sample.

In Step 340, the selected reading technique is used to determine the response of each analyte in the sample that is to be used in the ratio. Step 340 is referred to as reading the analyte (responses). Reading techniques that may be appropriate include: fluorescence, absorbance, reflectance, ion current, electrochemical potential, optical density, color, surface plasmon resonance, or others. The processing and reading techniques chosen usually depends on the nature of the sample and analytes to be measured. The response of the analytes measured using the chosen measurement method can be in any unit that is appropriate for the selected method. These units could be fluorescence units, optical density, color, ion current, chemiluminescence units, electrical signal, or others. The analytes can also be measured in a multiplexed format, where many analytes are measured in a single pass, or they can measured in multiple, but separate individual assays.

In step 350, the analyte responses are then converted into their corresponding concentrations. In one embodiment, the dose-response curves from step 240 of method 200 can be used. For example, the analyte response can be input into a formula of a dose-response curve to output the corresponding concentration.

In step 360, a dose surface model is used to obtain the analyte ratio from the concentrations. In one embodiment, the dose surface function from step 260 of method 200 can be used. For example, the concentrations can be input into a formula of a dose surface function to output the corresponding ratio. Therefore, some embodiments utilize the ratio of analyte doses that are determined indirectly, rather than directly from the responses.

In another embodiment, one of the two doses used to calculate the ratio is measured directly from a standard method, as opposed to using a dose-response curve. The other dose can be determined using the corresponding dose-reponse curve. For example 1, the percent A1c value can be based on a non-standard method such as immunoassay for the HbA1c concentration (Gc) and a standard optical density measurement for the total hemoglobin concentration (Tc). A dose surface regression model can be obtained between the ratio and the doses, one of which is converted from dose-response curve. These two doses can then be used, along with a dose surface function, to determine the corresponding ratio.

IV. Determing Concentration Using A Surface Model

As mentioned above, one embodiment can determine a concentration when the other concentration and the ratio of the analytes of the sample is known. For example, if the dose or level of a variable is to be measured, and this variable is in a known three-dimensional relationship with two other variables, the "dose-surface" model may be used for accurately measuring the first variable. In one embodiment, the dose surface model used to determine one of the concentrations can be the dose surface function obtained in step 260, but rearranged mathematically (e.g. using algebra) to provide the concentration as an output and to receive the other concentration and the ratio as input.

V. EXAMPLES

The following examples are provided to illustrate embodiments of the above methods.

A. Example 1

Example 1 is directed to embodiments for calculating the ratio from two concentrations, which are obtained using dose-response curves. Specifically, example 1 calculates the percent A1c value based on immunoassay for both the HbA1c concentration (Gc) and total hemoglobin concentration (Tc).

The %A1c value is defined as the percentage ratio between the concentration of the glycated hemoglobin, or hemoglobin A1c (Gc), and the concentration of the total hemoglobin (Tc), both of which are measured in this example using standard (or reference) methods:

$$\% A1c = 100 * Gc/Tc$$

The standard method for measuring Tc is using the optical density of the hemoglobin at 415 nm to calculate the concentration. The Gc is defined as the product of the Tc value and the %A1c value measured by another standard method, e.g. HPLC.

Establishing the two-curves and the dose surface model using calibrators is first discussed. In some embodiments, when new methods such as immunoassay are used for measuring both Gc and Tc, and hence percent HbA1c, a set of reference calibrators (or reference patient samples) carrying known %A1c (designated as %$A1c_k$), Gc (designated as $Gc_k$) and Tc (designated as $Tc_k$) values measured with standard methods are run first, as is described above for method 200. Based on the measured responses for hemoglobin A1c (Gr) and total hemoglobin (Tr) and the known doses ($Gc_k$ and $Tc_k$), two 4PL curves were obtained by fitting Gr and Tr against $Gc_k$ and $Tc_k$, respectively. From each 4PL curve, a pair of dose values (Gc and Tc) are obtained from the reverse 4PL curves for each pair of Gr and Tr (Equation A and B below). Based on the relationship of Gc and Tc values with the %$A1c_k$ value, a polynomial regression model is pre-selected and fit between %A1c (the ratio) and the Gc and Tc values. For example, the polynomial could be a constant plus other terms, each of which is a coefficient times a function (F) of Gc, Tc, or both.

Thus, the dose surface model can use a combination of three regression functions:

$Gc = c_g * (b_g/(Gr-a_g))^{(-1/d_g)}$:
dose-response curve      Equation A (reverse 4PL function:

$Tc = c_t * (b_t/(Tr-a_t))^{(-1/d_t)}$:
dose-response curve      Equation B (reverse 4PL function):

%$A1c = C0 + C1*(Gc/Tc) + C2*(Tc)^{(-0.4)}$: dose surface function      Equation C:

where a, b, c, d, C0, C1, and C2 are coefficients. In one aspect, at least four pairs of Gr and Tr data (i.e. responses from four samples) were used to determine the coefficients of the two 4PL curves. Once the coefficients are determined, the Gc and the Tc values can be calculated from the corresponding Gr and Tr values via each data response curve. At least three pairs of Gc and Tc values (the same samples used for determining the coefficients of the 4PL functions can be used) were used to determine C0, C1 and C2 in equation C. Once C0, C1 and C2 are fixed, the %A1c can be calculated directly from the Gr and Tr values by a combination of the three equations, e.g. substituting equations A and B into equation C.

To determine the coefficients, a plurality of data points are first determined. In this example, a set of 30 reference samples with known %$A1c_k$ values (determined by the Bio-Rad VARIANT II HPLC method), and known concentrations of total Hb and A1c ($Tc_k$ and $Gc_k$, respectively, in mg/mL, determined by the absorbance at 415 nm and the HPLC method) were selected. The %A1c values of the samples were evenly distributed across the range from 4.9% to 16.3%. Each sample was diluted to 1:1200 (or to an appropriate concentration). The 30 diluted sample tubes were placed on Bio-Plex 2200 (an automated, fluorescence-based multiplex immunoassay analyzer) for obtaining the measured fluorescent immunoassay response, Tr and Gr. Each sample was tested in duplicate. The %$A1c_k$ values ranged from about 4.9 to 16.3, the $Tc_k$ values ranged from about 109 to 191, and the $Gc_k$ values ranged from about 6.15 to 30 among the samples.

The coefficients were determined after fitting the regression model A, B and C using curve fitting. In this example, the coefficients were as follows:

$Gc = 217.6501*(128628.9/(Gr+1113.42))^{(1/1.10416)}$      Equation A (reverse 4PL function):

$Tc = 416.5246*(34909.31/(Tr+2657.328))^{(1/1.302901)}$      Equation B (reverse 4PL function):

%$A1c = 0.285999 + 0.957068*(Gc/Tc) + 0.276487033*(Tc)^{(-0.4)}$      Equation C:

If the reference samples in the above example are stable, they can be reused again. However, if the reference samples are scarce or unstable upon storage, this can be overcome by assigning values to a more stable, processed secondary calibrator set that can be stored and reused over time.

Obtaining Gr and Tr for the secondary calibrator set is now described. A set of 20 new, processed, stable secondary calibrators were prepared in such a way that they consisted of four levels of % A1c and five levels of total hemoglobin concentration (Tc). They were assayed as unknown patients in the same experiment with the reference samples serving as calibrators.

Calculating the Tc, Gc, and % A1c values for each secondary calibrator is now described. The measured Tr and Gr values were inserted into the dose response curves to obtain the Gc and Tc values. The % A1c values for the secondary calibrators were calculated using the Gc and Tc values that were inserted into equation dose surface function. The calculated Gc, Tc, and % A1c values for the secondary calibrators are values obtained from the regression models calculated from the reference samples.

The measured Tr and Gr values and the calculated Gc, Tc, and % A1c values were then used to re-determine the coefficients in the dose surface model using the secondary calibrators.

$$Gc = 87.71157 * (77934.74/(Gr + 1182.94))^{\wedge}(1/1.17804) \quad \text{Equation A (reverse 4PL function):}$$

$$Tc = 201.6066 * (21170.43/(Tr + 852.4913))^{\wedge}(1/2.284107) \quad \text{Equation B (reverse 4PL function):}$$

$$\% A1c = 0.923082 + 0.968838 * (Gc/Tc) - 5.029953915 * (Tc)^{\wedge}(-0.4) \quad \text{Equation C:}$$

Figure 4:
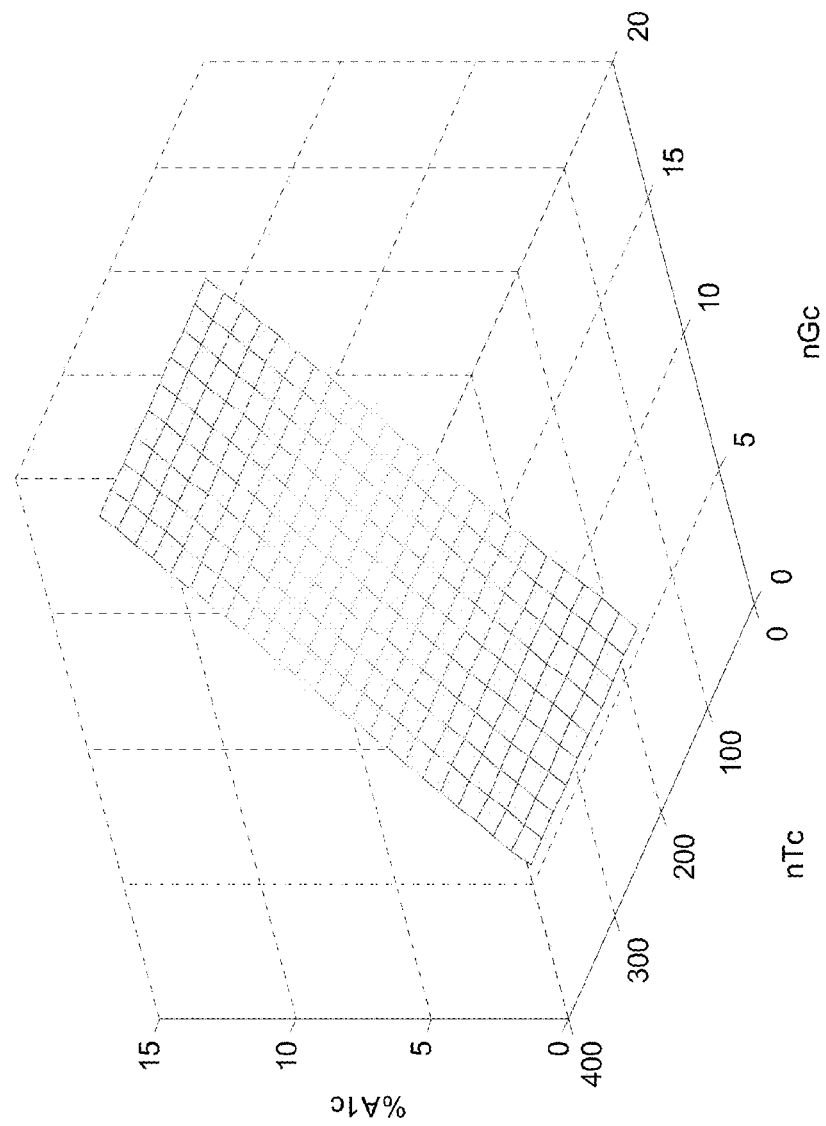
FIG. 4 shows a three-dimensional plot of a dose calibration surface according to embodiments of the present invention.

The new coefficients in models A, B and C can be stored on the same measuring device as long as the experimental and instrument conditions remain the same. If the experimental condition changes significantly, such as upon recalibration or upon a change of immunoassay reagents, this process of re-determining the coefficients can be repeated. FIG. 4 shows a 3-D plot of the dose calibration surface established by equation C.

The % A1c values of unknown patient samples were then calculated from the regression models obtained from the second calibrators. A set of unknown samples were assayed on the same instrument or measuring device. For each unknown sample, a pair of Tr and Gr values were obtained with the measuring device. The patient samples were also assayed by a reference HPLC method (Bio-Rad VARIANT II).

Figure 5:
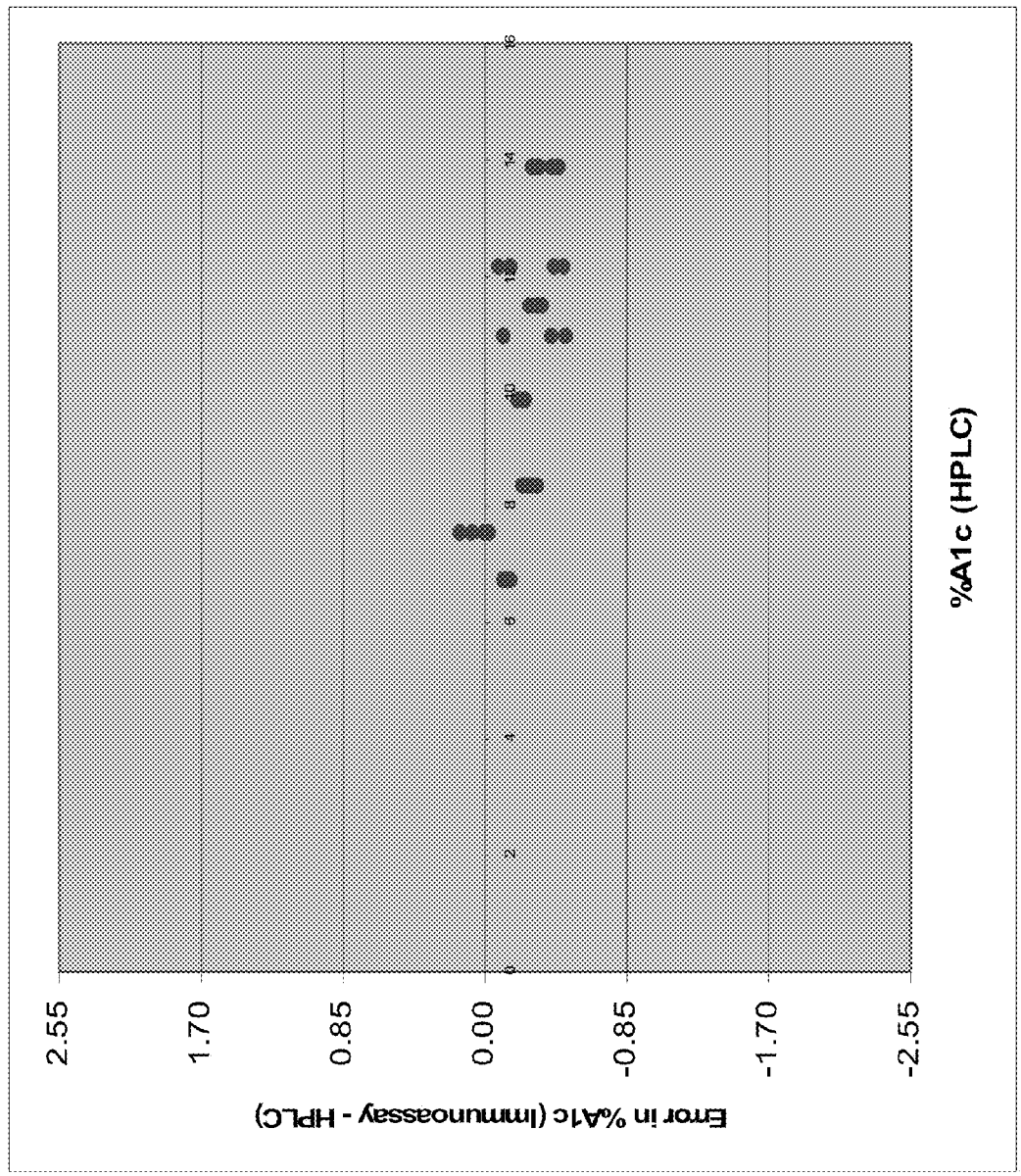
FIG. 5 is a plot in which the difference between the %A1c values shown on the Y-axis are plotted against the reference HPLC values on the X-axis according to embodiments of the present invention.

The Gr and Tr values were entered into the dose response curves. The calculated Gc and Tc values were entered into the dose surface function. The % A1c value was then calculated for each sample. The agreement between the calculated % A1c (from immunoassay) and the % A1c values measured by HPLC (the standard method) was demonstrated using a bias plot, in which the difference between the % A1c values between the two methods shown on the Y-axis, were plotted against the reference HPLC values on the X-axis, as shown in FIG. 5.

In this example, the 95% confidence interval (CI) of the difference between immunoassay and HPLC values (error) of the samples is 0.30%. The 95% confidence interval represents the precision of the all measured % A1c values across the relevant range. The smaller the number, the more precise the method. For example, for a hemoglobin A1c assay to obtain NGSP certification, the 95% confidence interval of the difference between the test and reference method must be less than 0.75% HbA1c in the range of 4-10% HbA1c. In one embodiment, a value of 0.75% (example of a threshold) or less is needed. The average of absolute differences as a percentage of each HPLC value (the averaged percentage error) is 2.31%. The percentage of patients with less than 10% error is 100%. The coefficient of variation (CV) of the replicates of the calculated % A1c values is 0.41. The averaged differences (grand mean), indicating the bias is −0.23%.

B. Example 2

This example compares the percent A1c value calculated as in example 1 with the percent A1c value determined using a "response surface" model. This example shows a comparison between the two methods for quantitation of results from patient samples run under two different experimental conditions.

The experimental conditions are as follows. Two immunoassay experiments, designated as Exp.1 and Exp.2 were performed at two different dates, separated by about two months, and utilizing different reagents for each assay. As a result, the responses for hemoglobin A1c and total hemoglobin (HbGr and HbTr, respectively) for the same sample were increased by nearly 100% from the Exp.1 to Exp.2. The calibrators used in Example 1 were used in both of these experiments. In each experiment, a set of fresh patient samples was used. Both sets of patient samples were quantitated in two ways, via a "response surface" calibration model and via a "dose surface" calibration model.

The "response surface" calibration model can be established that defines the target ratio (i.e. % A1c) based on the responses of the two ratio-defining variables (i.e. HbGr and HbTr). In order to understand model flexibility, a simple, non-transformed, polynomial regression was adopted. Based on the behavior of the patient samples, a 5-parameter model was pre-selected: Equation D: % A1c=C0+C1*(Gr/Tr)+C2*Gr+C3*Tr$^2$+C4*Gr$^2$/Tr, where the C0, C1, C2, C3 and C4 are coefficients.

The regression equation of the calibration model was established (i.e. the coefficients were determined) for both Exp.1 and 2, using the Gr and Tr values of the calibrators in each experiment and the same set of the known % A1c$_k$ values. The equation from each experiment was then used to calculate the % A1c values of the unknown patient samples in the same experiment. The "response surface" model was established by a secondary calibrator set. As in example 1, the secondary calibrator set first received assigned values from the reference sample set which was measured by standard methods. The reference sample set is the same set as in example 1. The Equation D was established was: % A1c=2.57+5.11*(Gr/Tr)+3.7*10$^{-4}$*Gr−1.5*10$^{-8}$*Tr$^2$−9.76*10$^{-6}$*Gr$^2$/Tr.

The secondary calibrator set was assigned % A1c values from this equation using the Gr and Tr values generated from Exp1. Based on the assigned % A1c values, the calibration surface equations (D) for the Exp1 and Exp2 by the secondary calibrator set are as follows:

$$\% A1c = 2.57 + 5.11*(Gr/Tr) + 3.7*10^{-4}*Gr - 1.53*10^{-8}*Tr^2 - 9.13*10^{-6}*Gr^2/Tr \quad \text{Exp1:}$$

$$\% A1c = 2.28 + 9.28*(Gr/Tr) + 8.6*10^{-5}*Gr - 3.4*10^{-9}*Tr^2 + 6.7*10^{-5}*Gr^2/Tr. \quad \text{Exp2:}$$

The "dose surface" calibration model was established (i.e. the coefficients were determined) for Exp1 and 2 using the Gr and Tr values of the calibrators in each experiment and the same set of the known % A1c$_k$ values. The equation from each experiment was then used to calculate the % A1c values of the unknown patient samples in the same experiment. Following the same steps in example 1 and using the same reference samples and the secondary calibrator set, the calibration surface equations (C) for the Exp1 and Exp2 by the secondary calibrator set were determined as follows:

$$\% A1c = 0.92308 + 0.96884*(Gc/Tc) - 5.02995*(Tc)^{\wedge}(-0.4) \quad \text{Exp1:}$$

%A1c=0.91036+0.97368*(Gc/Tc)−
5.0910*(Tc)^(−0.4).                                Exp2:

Quantitation of unknown patient samples in Exp1 and 2 was then determined. The unknown patient samples for Exp1 was the same as the sample set in Example 1. The unknown patient samples for Exp2 were different than for Exp1. The calculated %A1c values from the two surface models in Exp1 and 2 were compared against the simultaneously measured HPLC values the same way as in Example 1. The results are presented in FIG. 6.

Both of the two surface models were able to give good quantitation of the patient samples in Exp1 with low 1.96STD (95% CI), in the range of 0.3~0.33. But when the conditions changed to those in Exp2 (ie. the response of Tr increased about 100%), the "dose surface" calibration model was able to give a comparable 1.96STD, whereas the 1.96STD for the "response surface" calibration model was significantly higher (0.28 versus 1.08), suggesting greater robustness of the "dose surface" calibration model.

C. Example 3

This example uses data from exactly the same samples in the same experiment in Example 1, but uses different regression models according to embodiments of the present invention. The two dose-response curves and the dose surface model have the following functional form:

$$Gc=(b_g/(LnGr-a_g))^2 \quad \text{Equation A:}$$

$$Tc=(b_t/(LnTr-b_t))^2 \quad \text{Equation B:}$$

$$\%A1c=C0+C1*(Gc/Tc)+C2*(Tc)^{(-0.4)}+C3*(Gc/Tc)^{(4)} \quad \text{Equation C:}$$

where a, b, c, d, C0, C1, C2, and C3 are coefficients; and F1, F2, and F3 are functions of Gc and/or Tc. Once the coefficients are determined, the Gc and the Tc values can be calculated from the corresponding Gr and Tr values from each curve. At least four pairs of Gc and Tc values (the same samples used for determining the coefficients of the power functions can be used) were used to determine C0, C1, C2 and C3 in equation C. Once C0, C1, C2, and C3 are fixed, the %A1c can be calculated directly from the Gr and Tr values by a combination of the three equations by substituting the Gc and Tc values from A and B into Equation C, the combined equation model is $$\%A1c=C0+C1*((b_g/(LnGr-a_g))^2/(b_t/(LnGr-a_t))^2)+C2*((b_t/(LnGr-a_t))^2)^{(-0.4)}+C3*((b_g/(LnGr-a_g))^2/(b_t/(LnGr-a_t))^2)^{(4)}.$$

Using the above three equations, the secondary calibrators were assigned the values obtained as in example 1. The 20 secondary calibrators with the assigned values (AsgnTc$_k$s, AsgnGc$_k$ s and Asgn %A1c$_k$s) and their immunoassay responses established the regression models A, B and C:

$$Gc=(-9.68883/(LnGr-11.451))^2 \quad \text{Equation A:}$$

$$Tc=(-37.64607/(LnTr-11.79824))^2 \quad \text{Equation B:}$$

$$\%A1c=3.055288+0.979541*(Gc/Tc)-22.5058*(Tc)^{(-0.4)}-0.00000255969*(Gc/Tc)^{4} \quad \text{Equation C:}$$

The coefficients in models A, B and C can be stored on the same measuring device as long as the experiment condition is the same. In one embodiment, if the experimental condition changes significantly, the coefficients are re-determined.

Figure 7:
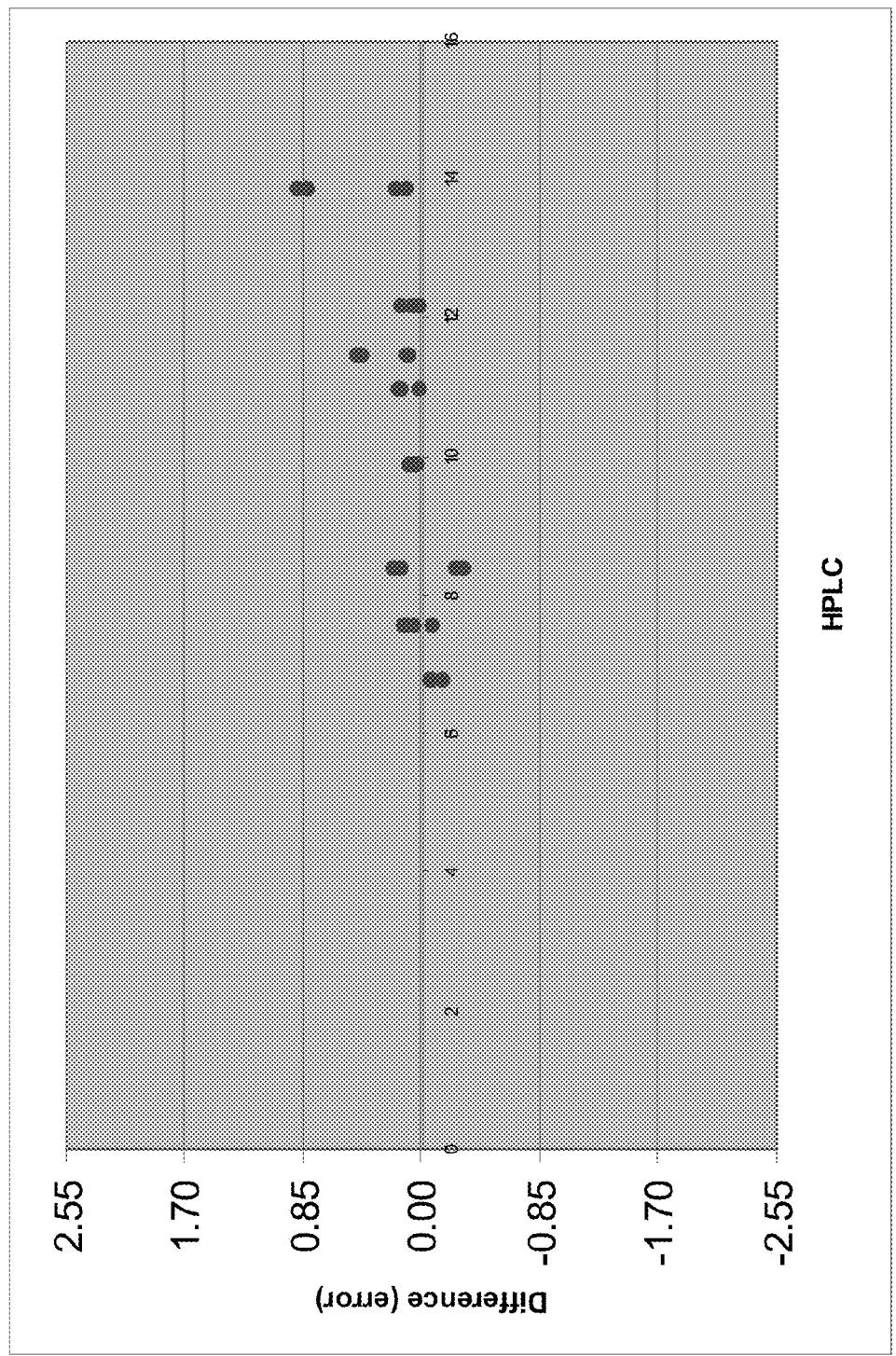
FIG. 7 is a plot in which the difference between the %A1c values shown on the Y-axis are plotted against the reference HPLC values on the X-axis according to embodiments of the present invention.

The %A1c values of unknown patient sample can then be calculated from the regression models. The information for the unknown patient samples are the same as Example 1. The Gr and Tr values were entered into equations A and B in step 1. The calculated Gc and Tc values were entered into equation C. The %A1c was then calculated for each sample. In order to compare the agreement between the calculated %A1c (from immunoassay) with the %A1c values measured by HPLC (the standard or reference method), the difference between the %A1c values from the two methods (shown on the Y-axis) were plotted as a function of the HPLC values (on the X-axis) shown in FIG. 7.

In this example, the 1.96 standard deviation (the 95% confidence interval) of the difference (or error) between immunoassay and HPLC values of the samples is 0.49%. The average percentage error (inaccuracy) is 1.70%. The percentage of patient with less than 10% error is 100%. The CV of the replicates of the calculated %A1c is 0.42. The averaged differences (grand mean), indicating the bias is −0.11%.

D. Example 4

If one uses two different methods to determine concentrations, then one can still use the surface method. For example, for immunoassay, one can use two-dimensional models for the immunoassay signal response, and then use the surface method. In another example, one can use high performance liquid chromatography (HPLC) to determine the concentrations, but still use the same non-linear surface function, even though the non-linear surface function may have been created from concentrations derived from the immunoassay. In one aspect, this is because the surface function uses concentrations, which are not device specific.

This example describes a use of a dose surface method for determining percent A1c assay using a format other than immunoassay according to embodiments of the present invention, specifically based on HPLC area measurements for both the HbA1c concentration (Gc) and total hemoglobin concentration (Tc). As in Example 1, percent A1c (%A1c) is defined as the direct ratio of the hemoglobin A1c (Gc) and total hemoglobin (Tc):

$$\%A1c=100*Gc/Tc$$

in which, the Tc is determined by a standard method for measuring using the optical density (OD) of hemoglobin at 415 nm for calculation of the concentration. The standard %A1c value is obtained from a standard HPLC method (in which the exact measuring procedure may vary, but is referenced to an international standard). The standard Gc in this example is defined as the product of the Tc value and the %A1c value measured by the HPLC standard method using the formula:

$$\%A1c=100*Gc/Tc.$$

The non-standard assay method in this example measures the Gc and Tc values not via absorbance, but via the peak areas for the hemoglobin A1c and the total hemoglobin from the HPLC trace. The peak areas for the hemoglobin A1c and the total hemoglobin become the Gr and Tr values. In a calibration event, two dose-response curves can be established between the doses (Gc and Tc via the standard method) and the responses (peak areas of Gr and Tr). The %A1c value calculated by the direct ratio of Gc to Tc derived from the HPLC peak areas (the "two curve" method) can be biased by the size of the peak area for Tr. Therefore a dose surface method can be applied in this case to improve the accuracy of the result.

A set of reference calibrators (or reference patient samples) carrying known %A1c (designated as %A1c$_k$), Gc (designated as Gc$_k$) and Tc (designated as Tc$_k$) values measured with standard methods are run first. Based on the analysis of the behavior of the measured peak areas (Gr and Tr) to the known doses ($Gc_k$ and $Tc_k$), two 4PL curves are obtained by fitting the Gr and Tr against the $Gc_k$ and $Tc_k$, respectively. From each 4PL curve, a pair of dose values (Gc and Tc) are obtained from the reverse 4PL curves for each pair of Gr and Tr (Equation A and B below). Based on the analysis of the behavior of the Gc and Tc values in relation to the % $A1c_k$ value, a polynomial regression model (Equation C) is fit between % A1c and the variables: (Gc/Tc), $(Tc)^{-3}$ and $(Gc/Tc)^9$.

Thus, the Dose Surface Model uses a combination of 3 regression functions:

$$Gc=c_g*(b_g/(Gr-a_g)-1)^{\wedge}(1/d_g) \quad \text{Equation A (reverse 4PL function):}$$

$$Tc=c_t*(b_t/(Tr-a_t)-1)^{\wedge}(1/d_t) \quad \text{Equation B (reverse 4PL function):}$$

$$\%\ A1c=i\ C0+C1*(Gc/Tc)+C2*(Tc)^{\wedge}(-3)+C3*(Gc/Tc)^{\wedge}9 \quad \text{Equation E:}$$

where a, b, c, d, C0, C1, and C2 are coefficients. At least four pairs of Gr and Tr data (ie. responses from four samples) were used to determine the coefficients of the two 4PL curves. Once the coefficients are determined, the Gc and the Tc values can be calculated from the corresponding Gr and Tr values from each curve. At least four pairs of the Gc and Tc values (the same samples used for determining the coefficients of the 4PL functions can be used) were used determine C0, C1, C2, and C3 in equation C. Once the C0, C1, C2, and C3 are fixed, the % A1c can be calculated directly from the Gr and Tr values by a combination of the three equations as follows:

By substituting the Gc and Tc in A and B into Equation C, the combined equation (model) is:

$$\% A1c = C0+C1*((c_g*(b_g/(Gr-a_g)-1)^{\wedge}(1/d_g))/(c_t*(b_t/(Tr-a_t)-1)^{\wedge}(1/d_t)))+C2*(c_t*(b_t/(Tr-a_t)-1)^{\wedge}(1/d_t)^{\wedge}(-3)+C3*((c_g*(b_g/(Gr-a_g)-1)^{\wedge}(1/d_g))/(c_t*(b_t/(Tr-a_t)-1)^{\wedge}(1/d_t)))^{\wedge}9$$

The reference calibrators were then run in the immunoassay. A set of 25 reference samples with known % $A1c_k$ value (determined by the Bio-Rad VARIANT II HPLC method), the concentration of total Hb, and hemoglobin A1c ($Tc_k$ and $Gc_k$, in mg/mL, determined by OD at 415 nm and the HPLC method) were selected. The % A1c values of the samples were evenly distributed across the range from 5% to 16.4%. Each sample was diluted to 1:300 (or to an appropriate concentration). The 25 diluted sample tubes were placed on a Bio-Rad VARIANT II instrument for obtaining the measured peak areas, Tr and Gr.

The coefficients can be determined after fitting the regression model A, B and E using any curve fitting software. The final equations are:

$$Gc=54120.48*(4.48\times10^{\wedge}8/(Gr-5856.218)-1)^{\wedge}(-1/1.02992) \quad \text{Equation A (reverse 4PL function):}$$

$$Tc=589.3859*(6592211/(Tr-224577.4)-1)^{\wedge}(-1/1.474962) \quad \text{Equation B (reverse 4PL function):}$$

$$\% A1c=0.730394133+0.950950363*(Gc/Tc)-142374.986*(Tc)^{\wedge}(-3)-4.28589E-12*(Gc/Tc)^{\wedge}9 \quad \text{Equation E:}$$

The % A1c values of unknown patient sample were calculated from the regression models. A set of unknown samples were assayed on the same HPLC as the reference calibrators in step1. For each unknown sample, a pair of Tr and Gr (peak area) values were obtained. The patient samples were also assayed by HPLC separately using the standard method. The unknown samples were assayed by both the standard HPLC method and the non-standard peak area method defined in this example.

Figure 8:
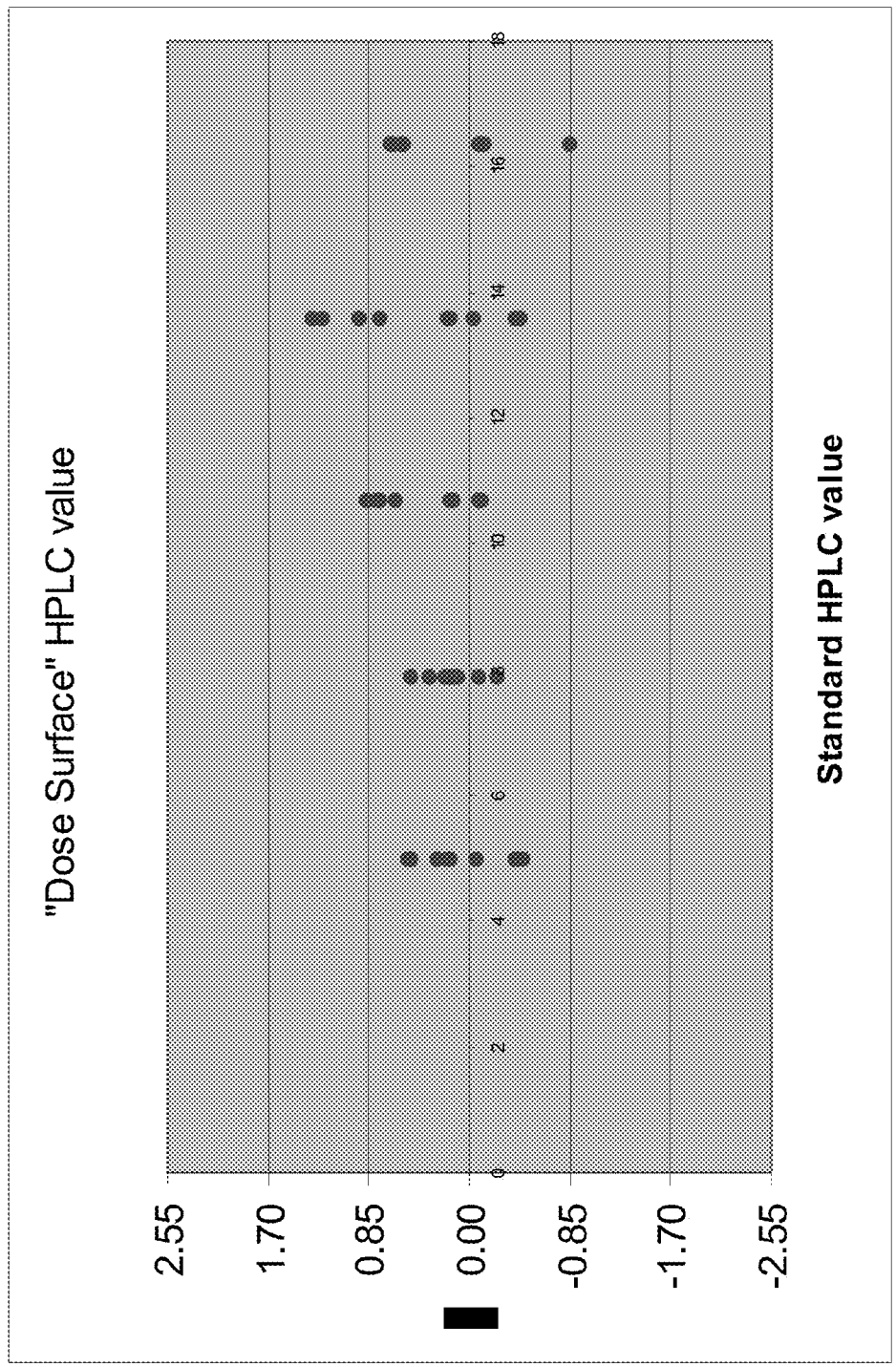
FIG. 8 is a plot in which the difference between the %A1c values shown on the Y-axis are plotted against the reference HPLC values on the X-axis according to embodiments of the present invention.

The Gr and Tr values were entered into equations A and B. The calculated Gc and Tc values were plugged into Equation E. The % A1c was then calculated for each sample. In order to compare the agreement between the calculated % A1c (from peak area) with the % A1c values measured by HPLC standard method, the difference between the % A1c values from the two methods (Y-axis) were plotted against the standard HPLC values (X-axis) shown in FIG. 8.

In this example, the 1.96 standard deviation (the 95% confidence interval) of the difference (or error) between immunoassay and HPLC values of the samples is 0.89%. The average of absolute differences as a percentage of each HPLC value (the averaged percentage error) is 4.06%. The percentage of patient with less than 10% error is 100%. The CV of the replicates of the calculated % A1c is 2.0. The averaged differences (grand mean), indicating the bias is 0.23%.

This result is better than the "two curve" method which calculates the % A1c via 100*Gc/Tcm which provides as follows. The 1.96 standard deviation (the 95% confidence interval) of the difference (or error) between immunoassay and HPLC values of the samples is 1.91%. The average of absolute differences as a percentage of each HPLC value (the averaged percentage error) is 5.90%. The percentage of patient with less than 10% error is 80%. The CV of the replicates of the calculated % A1c is 2.36. The averaged differences (grand mean), indicating the bias is 0.44%.

E. Example 5

This example is directed to embodiments from section IV above. Instead of calculating a ratio, this example utilizes a dose calculation for hemoglobin A1c (Gc) in which the response (Gr) is subject to interference by another variable, in this case total hemoglobin (Tc). The reference method for calculating hemoglobin A1c (Gc) in this example is defined as Gc=% A1c*Tc/100, in which % A1c is determined by HPLC, and the total hemoglobin (Tc) is determined by absorbance at 415 nm. The non-standard method used for calculating Gc in this example is immunoassay. Because of interference from Tc, the direct calculation of the dose of glycated hemoglobin (Gc) from the dose-response curve (Gc-Gr) would produce an inaccurate result. The result is termed $Gc_{Apparent}$. By studying the patterns of the responses (Gr and Tr), we found that the Gc is in a surface relationship with multiple combinations of the $Gc_{Apparent}$ and Tc calculated from the dose-response curves Gc-Gr and Tc-Tr. Thus, in this embodiment, the actual Gc is the proportion of $Gc_{Apparent}$ and Tc.

The dose surface model uses a combination of three regression functions:

$$Gc_{Apparent}=c_g*(b_g/(Gr-a_g)-1)^{\wedge}(1/d_g) \quad \text{Equation A (reverse 4PL function):}$$

$$Tc=c_t*(b_t/(Tr-a_t)-1)^{\wedge}(1/d_t) \quad \text{Equation B (reverse 4PL function):}$$

$$Gc=C0+C1*Gc_{Apparent}+C2*(Tc)^{\wedge}(-1)+C3*(Gc_{Apparent}/Tc) \quad \text{Equation F:}$$

where a, b, c, d, C0, C1, C2 and C3 are coefficients. Once the coefficients are determined, the $Gc_{Apparent}$ and the Tc values can be calculated from the corresponding Gr and Tr values from each curve. At least four pairs of Gc and Tc (the same samples used for determining the coefficients of the power functions can be used) are used to determine C0, C1, C2, and C3 in equation C. Once C0, C1, C2, and C3 are fixed, Gc can be calculated directly from the Gr and Tr values by a combination of the three equations by substituting Gc and Tc in A and B into Equation C:

$$Gc=C0+C1*((c_g*(b_g/(Gr-a_g)-1)^\wedge(1/d_g))+C2*(c_t*(b_t/(Tr-a_t)-1)^\wedge(1/d_t)^\wedge(-1)+C3*((c_g*(b_g/(Gr-a_g)-1)^\wedge(1/d_g))/(c_t*(b_t/(Tr-a_t)-1)^\wedge(1/d_t)))$$

The established regression models A, B and F resulting from a fitting are:

$$Gc_{Apparent}=29.859*(28650.74/(Gr\ 557.56)-1)^\wedge(-1/-1.8469) \quad \text{Equation A (reverse 4PL function):}$$

$$Tc=649.35*(75834.99/(Tr-3217.46)-1)^\wedge(-1/1.278) \quad \text{Equation B (reverse 4PL function):}$$

$$Gc=0.756140684+0.780449528*Gc_{Apparent}-1.506283809*(Tc)^\wedge(-1)+0.378402501*(Gc_{Apparent}/TC) \quad \text{Equation F:}$$

The coefficients in models A, B and F can be stored on the same measuring device as long as the experiment condition is the same. In one embodiment, if the experimental condition changes significantly, the coefficients can be re-determined.

Figure 9:
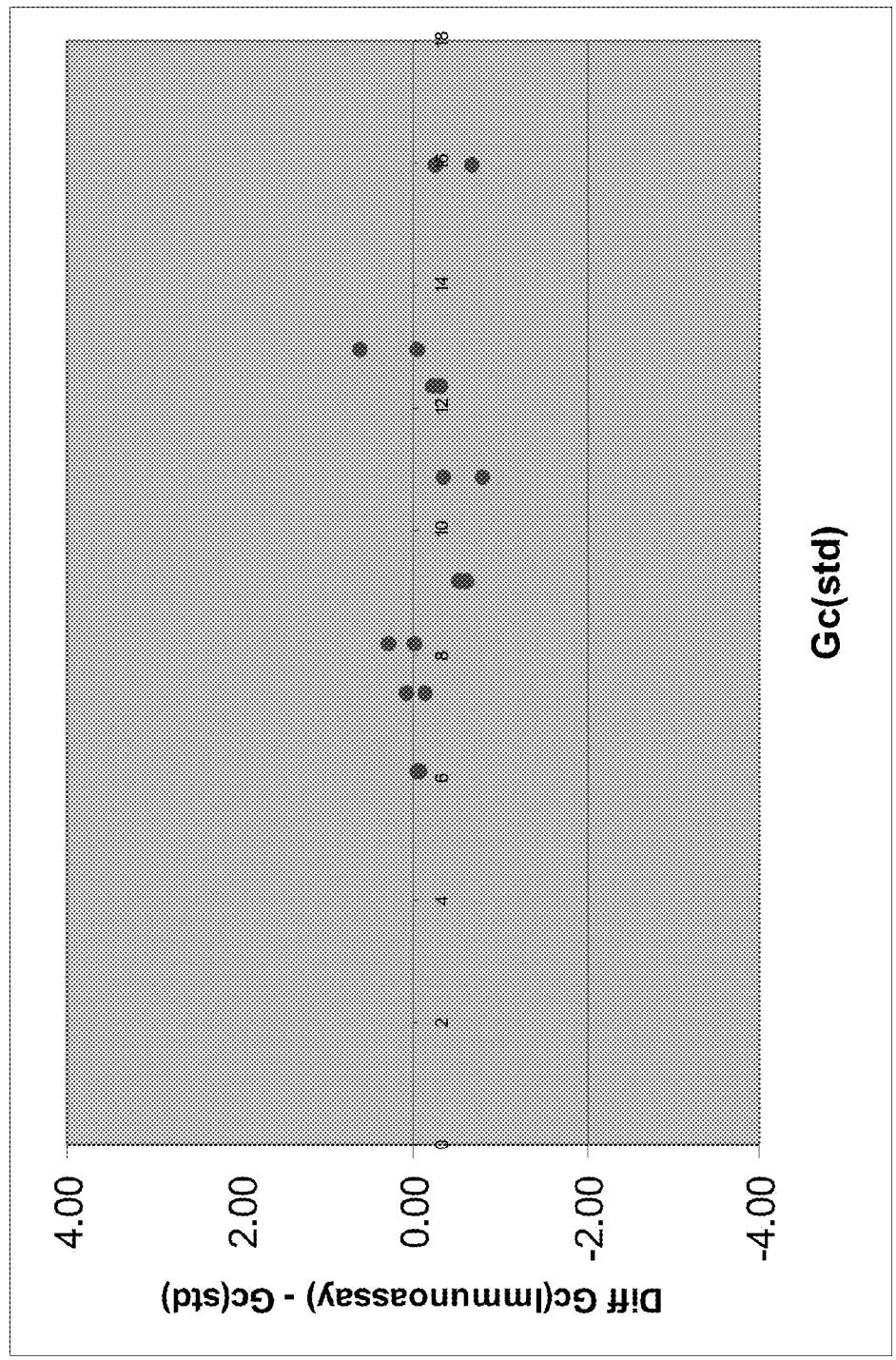
FIG. 9 is a plot showing the agreement between the Gc calculated according to embodiments of the present invention and a standard method.

The Gc values of unknown patient sample are calculated from the regression models above. The Gc values were measured with standard method separately. In order to compare the agreement between the Gc calculated from the immunoassay and the standard method, the difference between the Gc values from the two methods (on Y-axis) were plotted along the standard method values (on X-axis) shown in FIG. 9.

In this example, the 1.96 standard deviation (the 95% confidence interval) of the difference (or error) between immunoassay and standard values is 0.72 (mg/mL). The averaged percentage error (inaccuracy) is 2.64%. The percentage of patient with less than 10% error is 100%. The CV of the replicates of the calculated Gc is 1.79. The averaged differences (grand mean), indicating the bias is −0.21 mg/ml.

In one embodiment, the value for Gc can be considered a proportion of the concentrations $Gc_{Apparent}$ and Tc. Note this method may be used for any concentrations. In one implementation, the values for Gc and Tc can then be used to determine a proportion of Gc and Tc (e.g. % A1c).

Figure 10:
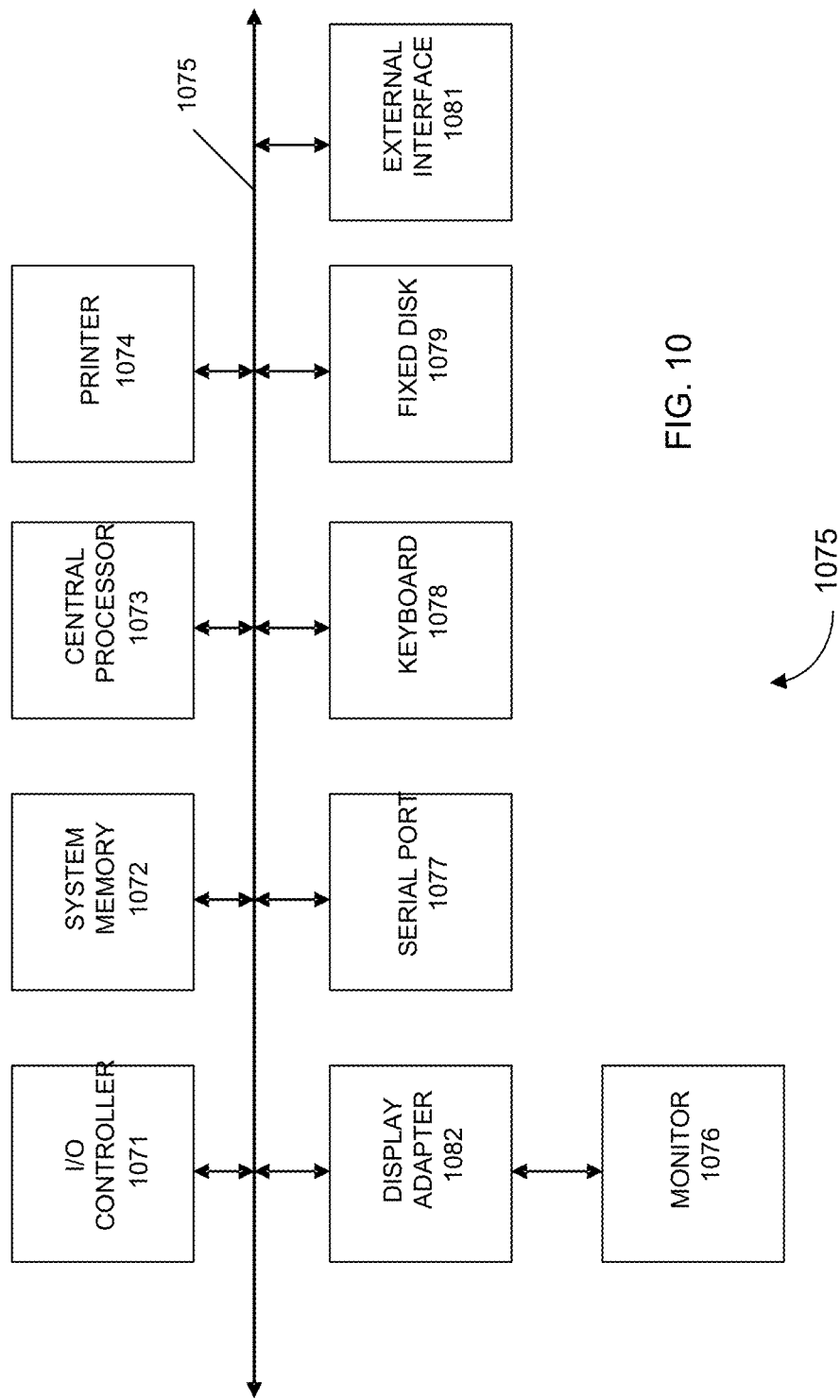
FIG. 10 shows a block diagram of an example computer system usable with system and methods according to embodiments of the present invention.

Any of the computer systems mentioned herein may utilize any suitable number of subsystems. Examples of such subsystems are shown in FIG. 10 in computer apparatus 1000. In some embodiments, a computer system includes a single computer apparatus, where the subsystems can be the components of the computer apparatus. In other embodiments, a computer system can include multiple computer apparatuses, each being a subsystem, with internal components.

The subsystems shown in FIG. 10 are interconnected via a system bus 1075. Additional subsystems such as a printer 1074, keyboard 1078, fixed disk 1079, monitor 1076, which is coupled to display adapter 1082, and others are shown. Peripherals and input/output (I/O) devices, which couple to I/O controller 1071, can be connected to the computer system by any number of means known in the art, such as serial port 1077. For example, serial port 1077 or external interface 1081 can be used to connect computer system 1000 to a wide area network such as the Internet, a mouse input device, or a scanner. The interconnection via system bus 1075 allows the central processor 1073 to communicate with each subsystem and to control the execution of instructions from system memory 1072 or the fixed disk 1079, as well as the exchange of information between subsystems. The system memory 1072 and/or the fixed disk 1079 may embody a computer readable medium. Any of the values mentioned herein can be output from one component to another component and can be output to the user.

A computer system can include a plurality of the same components or subsystems, e.g., connected together by external interface 1081. In some embodiments, computer systems, subsystem, or apparatuses can communicate over a network. In such instances, one computer can be considered a client and another computer a server. A client and a server can each include multiple systems, subsystems, or components, mentioned herein.

Figure 11:
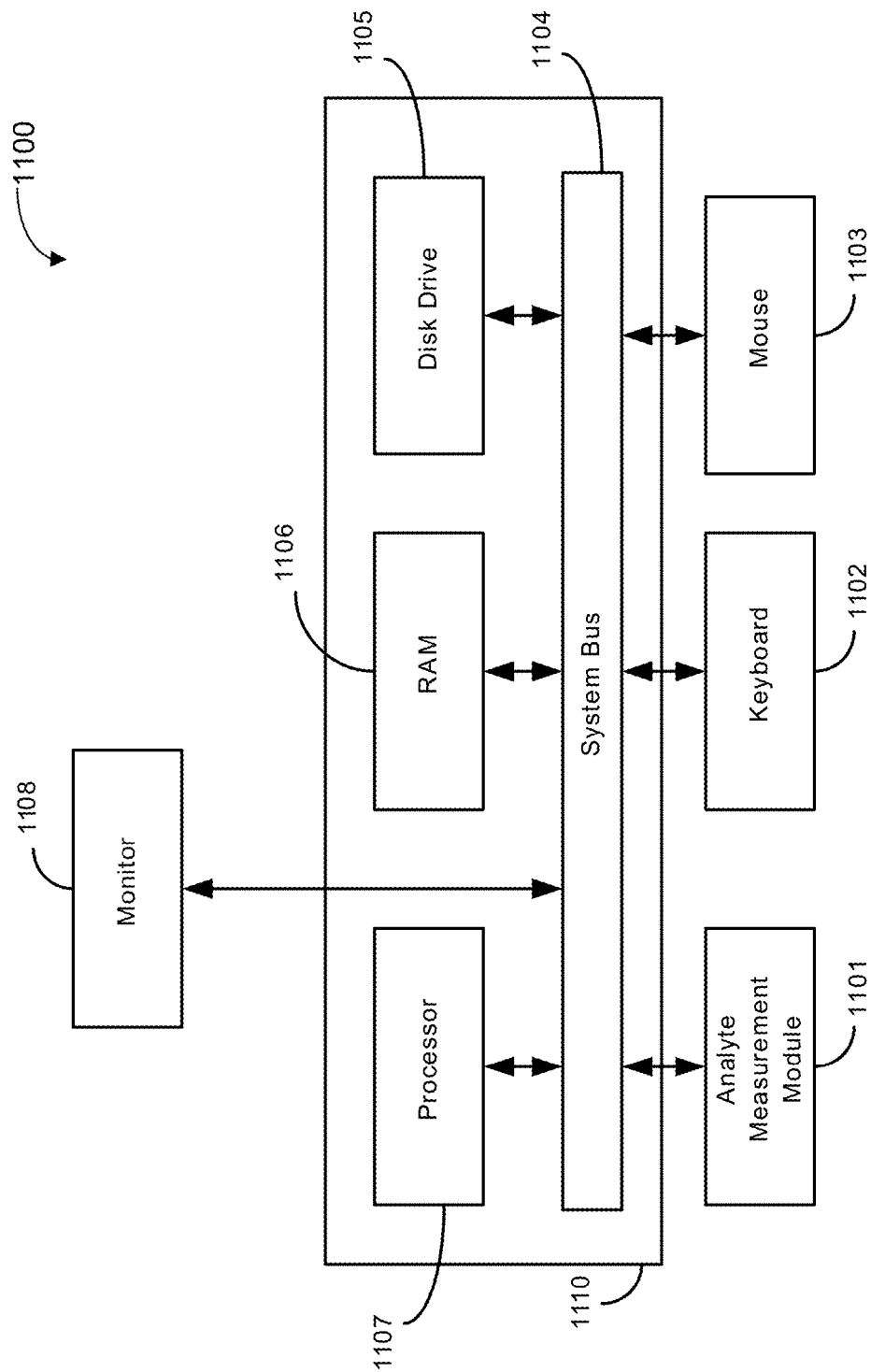
FIG. 11 is a block diagram of an apparatus for determining one or more properties of a biological sample according to embodiments of the present invention.

FIG. 11 is a block diagram of an apparatus 1100 that can be used to execute any of the embodiments of the invention. Apparatus 1100 include a computer system 1110 and has a number of input modules. An analyte measurement module 1101 is used to measure the analyte responses in a test sample. This module can vary between different embodiments of the invention depending on the measurement method selected to measure the analyte responses. Also shown are a standard keyboard 1102 and mouse 1103. Apparatus 1100 can also contains a variety of typical computer components inside computer system 110. These components can include a system bus 1104, one or more disk drives 1105, RAM 1106, and a processor 1107. FIG. 11 also shows a monitor 1108 that allows information to be displayed to a user of the system. Other components can also be present depending on the exact nature of the embodiment. In various embodiments, the apparatus can include any of the features of computer system 1000.

In one embodiment of the invention, the pre-processed sample that was created as in step 320 is placed in the analyte measurement module 1101 where the sample is further processed and the analyte responses in the sample are measured. This information is then transferred into the computer system along a system bus 1104, and an appropriate conversion method is applied to the analyte response data using the processor 1107. The instructions the processor 1107 executes to implement instructions for any methods described herein, where the instruction can be stored on a computer readable medium such as the RAM 1106 or disk drive 1105. The results from the methods can then be displayed on the monitor 308. Alternative embodiments of the invention can output results (e.g. the analyte ratio) using other communications means. For example, the computer system could print the measured ratio using a printer or send the measured ratio to another computer over a network.

The specific details of particular embodiments may be combined in any suitable manner without departing from the spirit and scope of embodiments of the invention. However, other embodiments of the invention may be directed to specific embodiments relating to each individual aspect, or specific combinations of these individual aspects.

It should be understood that any of the embodiments of the present invention can be implemented in the form of control logic using hardware and/or using computer software in a modular or integrated manner. Based on the disclosure and teachings provided herein, a person of ordinary skill in the art will know and appreciate other ways and/or methods to implement the present invention using hardware and a combination of hardware and software.

Any of the software components or functions described in this application may be implemented as software code to be executed by a processor using any suitable computer language such as, for example, Java, C++ or Perl using, for example, conventional or object-oriented techniques. The software code may be stored as a series of instructions or commands on a computer readable medium for storage and/ or transmission, suitable media include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium according to an embodiment of the present invention may be created using a data signal encoded with such programs. Computer readable media encoded with the program code may be packaged with a compatible device or provided separately from other devices (e.g., via Internet download). Any such computer readable medium may reside on or within a single computer program product (e.g. a hard drive, a CD, or an entire computer system), and may be present on or within different computer program products within a system or network. A computer system may include a monitor, printer, or other suitable display for providing any of the results mentioned herein to a user.

The above description of exemplary embodiments of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications to thereby enable others skilled in the art to best utilize the invention in various embodiments and with various modifications as are suited to the particular use contemplated.

What is claimed is:

1. A method comprising:
measuring a first response for a first analyte in a biological sample;
calculating, by a computer system, a first concentration using the first response and a first regression function that maps the first response to the first concentration;
receiving a second concentration for a second analyte of the biological sample
receiving a non-linear function that maps the first and second concentrations to a proportion of the first and second concentrations in the biological sample; and
calculating, by the computer system, the proportion using the non-linear function and the first and second concentrations.

2. The method of claim 1, further comprising:
using the proportion to provide diagnostic information for a patient from whom the biological sample was obtained.

3. The method of claim 1, wherein the first concentration is for A1c, the second concentration is for total hemoglobin, and the proportion is the percentage of A1c per amount of hemoglobin.

4. The method of claim 1, further comprising:
calculating the non-linear function using samples with known first and second concentrations and known proportions, wherein the non-linear function is obtained from one or more regressions using the known concentrations and proportion values.

5. The method of claim 4, further comprising:
measuring first and second signal responses of calibration samples with known corresponding first and second concentrations, thereby providing a first and a second set of dose-response data points;
calculating a first dose-response function that approximates the relation between the first signal responses and the first concentration, wherein calculating the first dose-response function uses the first set of dose-response data points; and
calculating a second dose-response function that approximates the relation between the second signal responses and the second concentration, wherein calculating the second dose-response function uses the second set of dose-response data points.

6. The method of claim 1, further comprising:
mathematically transforming the first response; and
using the transformed first response as an input to the first regression function to calculate the first concentration.

7. The method of claim 1, wherein the second concentration is obtained from a reference method that obtains the concentration through a direct measurement.

8. The method of claim 1, further comprising:
determining the first regression function using a plurality of samples whose first concentrations are known.

9. The method of claim 1, wherein the non-linear function is received from a computer readable medium at a processor of the computer system.

10. A computer program product comprising a non-transitory computer readable medium storing a plurality of instructions for controlling a processor to perform an operation for obtaining a property of a biological sample, the instructions comprising:
calculating a first concentration using a measured first response for a first analyte in a biological sample and a first regression function that maps the first response to the first concentration;
receiving a second concentration for a second analyte of the biological sample
receiving a non-linear function that maps the first and second concentrations to a proportion of the first and second concentrations in the biological sample; and
calculating the proportion using the non-linear function and the first and second concentrations.

11. An apparatus for obtaining a property of a biological sample, the apparatus comprising:
a measuring module capable of measuring responses of analytes in a biological sample;
a memory to store the measured analyte responses from the measuring module;
a non-transitory computer readable medium storing a plurality of instructions, the instructions comprising:
calculating a first concentration using a measured first response of a first analyte and a first regression function that maps the first response to the first concentration;
receiving a second concentration for a second analyte of the biological sample;
receiving a non-linear function that maps the first and second concentrations to a proportion of the first and second concentrations in the biological sample; and
calculating the proportion using the non-linear function and the first and second concentrations; and
a processor to execute the computer readable instructions on the computer readable medium in order to calculate the proportion.

12. The method of claim 1, further comprising:
measuring a second response for the second analyte in the biological sample; and
calculating, by the computer system, the second concentration using the second response and a second regression function that maps the second response to the second concentration.

13. A method comprising:
- measuring a first response for a first analyte in a biological sample;
- calculating, by a computing system, a first concentration using the first response and a first regression function that maps the first response to the first concentration;
- receiving a proportion of the first analyte and the second analyte of the biological sample;
- receiving a second regression function that maps the first concentration and the proportion to a second concentration of the second analyte in the biological sample; and
- calculating, by the computing system, the second concentration using the second regression function, the first concentration, and the proportion.

* * * * *